(12) United States Patent
Endo et al.

(10) Patent No.: US 8,599,805 B2
(45) Date of Patent: Dec. 3, 2013

(54) WIRELESS COMMUNICATION TERMINAL

(75) Inventors: Takahisa Endo, Tokyo (JP); Ryohei Kagawa, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 162 days.

(21) Appl. No.: 13/158,028

(22) Filed: Jun. 10, 2011

(65) Prior Publication Data

US 2011/0243116 A1 Oct. 6, 2011

Related U.S. Application Data

(63) Continuation-in-part of application No. PCT/JP2009/070752, filed on Dec. 11, 2009.

(30) Foreign Application Priority Data

Dec. 12, 2008 (JP) .................................. 2008-317400

(51) Int. Cl.
*H04W 4/00* (2009.01)

(52) U.S. Cl.
USPC ........... 370/338; 370/337; 370/345; 370/347; 370/350; 370/458; 455/427; 455/428; 455/439; 455/440; 455/445; 455/512; 455/525; 455/517

(58) Field of Classification Search
None
See application file for complete search history.

(56) References Cited

U.S. PATENT DOCUMENTS

| | | | | |
|---|---|---|---|---|
| 5,771,352 | A * | 6/1998 | Nakamura et al. | 709/227 |
| 5,966,658 | A * | 10/1999 | Kennedy et al. | 455/426.1 |
| 6,678,341 | B1 * | 1/2004 | Miyake et al. | 375/356 |
| 2001/0026553 | A1 * | 10/2001 | Gallant et al. | 370/395 |
| 2006/0206592 | A1 | 9/2006 | Fujii et al. | |
| 2007/0038023 | A1 | 2/2007 | Uchimura et al. | |
| 2008/0141319 | A1 * | 6/2008 | Jang et al. | 725/105 |
| 2010/0074446 | A1 * | 3/2010 | Fuchs et al. | 380/278 |

FOREIGN PATENT DOCUMENTS

| | | |
|---|---|---|
| CN | 1215293 A | 4/1999 |
| CN | 2706123 Y | 6/2005 |
| CN | 1960669 A | 5/2007 |
| CN | 100399758 C | 7/2008 |
| JP | 60-4811 A | 1/1985 |
| JP | 2004-328269 A | 11/2004 |
| JP | 2006-280828 A | 10/2006 |

OTHER PUBLICATIONS

International Search Report of PCT/JP2009/070752, mailing date Mar. 16, 2010.
Extended European Search Report dated Feb. 5, 2013, issued in corresponding European Patent Application No. 09831965.0.
Chinese Office Action dated May 20, 2013, issued in corresponding Chinese Patent Application No. 200980148619.4, w/ English translation.

* cited by examiner

*Primary Examiner* — Ian N Moore
*Assistant Examiner* — Eric H Wang
(74) *Attorney, Agent, or Firm* — Westerman, Hattori, Daniels & Adrian, LLP

(57) ABSTRACT

A wireless communication terminal that performs wireless communication with other terminal includes an information holding unit that holds a communication channel setting of the wireless communication and information of a communication attribute of the wireless communication, a communication unit that receives the information of the communication attribute held by the other terminal from the other terminal by wireless communication using a communication channel that the communication channel setting held by the information holding unit represents before a logical connection of the wireless communication with the other terminal is established, and a control unit that controls the establishment process of the logical connection with the other terminal based on the information of the communication attribute received by the communication unit.

3 Claims, 9 Drawing Sheets

FIG. 7

| CH SWITCH NUMBER | COMMUNICATION SETTING | | |
|---|---|---|---|
| | FREQUENCY CHANNEL | SSID | WEP |
| 1 | 1 | ID_A | WEP1 |
| 2 | 6 | ID_B | WEP2 |
| 3 | 12 | ID_C | WEP3 |

FIG. 8A

| MAC Header (Probe Request) | SSID | Supported Rates | FCS |
|---|---|---|---|
| 800 | 801 | 802 | 803 |

FIG. 8B

| MAC Header (Probe Response) | SSID | COMMUNICATION ATTRIBUTE | Supported Rates | FCS |
|---|---|---|---|---|
| 810 | 811 | 812 | 813 | 814 |

WIRELESS COMMUNICATION TERMINAL

TECHNICAL FIELD

The present invention relates to a wireless communication terminal that performs wireless communication by a wireless communication technique such as a wireless local area network (LAN).

This application claims priority based on Japanese Patent Application No. 2008-317400 filed on Dec. 12, 2008, the disclosure of which is incorporated herein by reference.

BACKGROUND ART

In recent years, an endoscopic device that inserts a slender insert section into a body cavity or a conduit and observes a subject image inside the body cavity or the conduit through a monitor has been widely used. The endoscopic device generally includes an endoscope having the insert section that is inserted into the body cavity or the conduit and a body device having a light source device and a video processor. The endoscope and the body device are connected to each other by a light guide cable that guides illumination light from the light source device to the endoscope and a signal cable that transmits an imaging signal obtained by the endoscope to the video processor. This limits a movement range of the endoscope and hampers operability of the endoscope.

For example, in Patent Document 1, by installing an illuminating device configured by a light emitting diode (LED) or the like in the endoscope, the light guide cable extending from the endoscope is removed. Further, a video signal processing circuit that performs a video signal process on the imaging signal to acquire a video signal that can be displayed on the monitor and a transmission circuit that transmits the video signal through radio waves are installed in the endoscope. A receiving device that receives radio waves and demodulates the video signal is installed separately from the endoscope, and thus the signal cable extending from the endoscope is removed. Such an endoscopic device is generally referred to as a wireless endoscopic device and has an advantage in that the limitation of the movement range of the endoscope decreases and the operability is improved.

PRIOR ART DOCUMENT

Patent Document

[Patent Document 1] Japanese Patent Application, First Publication No. S60-4811

DISCLOSURE OF THE INVENTION

Problems to be Solved by the Invention

In a conventional wireless endoscopic device, a receiving device is installed separately from an endoscope. For this reason, it is necessary to perform setting of a communication channel of the endoscope at a transmission side according to a communication channel set for the receiving device and perform a connection through wireless communication. A technique of uniquely deciding a combination of the receiving device and the endoscope and fixedly setting a communication channel to an arbitrary channel in advance may be considered. However, in a hospital that uses a plurality of receiving devices and a plurality of endoscopes, disinfection, sterilization and the inspection of the endoscopes are simultaneously performed. Therefore, the combination of the receiving device and the endoscope is not uniquely decided. Further, in order to prevent interference of radio waves, it is necessary to differentially set the communication channels of the receiving devices.

To this end, a switch for selecting the communication channel is installed in each of the receiving device and the endoscope. As a result, when the endoscopic device comes into use, the same communication channel as the communication channel set for the receiving device of a use target is set for the endoscope of a use target, and the receiving device and the endoscope are connected with each other by wireless communication. For example, as illustrated in FIG. 10, when receiving devices 1 and 2 are installed in medical examination rooms A and B, respectively, and different communication channels are set for the respective receiving devices, an endoscope 3 can normally be wirelessly connected to the receiving device 1.

However, as illustrated in FIG. 11, due to an operator's setting mistake, the same communication channel as the receiving device 1 of the medical examination room A may be set for the receiving device 2 installed in the medical examination room B, or the same communication channel as the communication channel set for the receiving device 1 may be set for the endoscope 3 and a wireless connection may start. In this case, the receiving device 2 of the medical examination room B is wirelessly connected. As a result, there arises a problem in that the endoscope 3 and the receiving device 1 are not normally wirelessly connected with each other as intended.

Further, as illustrated in FIG. 12, the receiving device 1 and the receiving device 2 are installed outside a range in which wireless communication can be mutually performed. However, if the receiving devices 1 and 2 are located within a wireless communication range of the endoscope 3, there arises a problem in that the endoscope 3 is erroneously connected with the receiving device 2. Further, as illustrated in FIG. 13, when endoscopes 3 and 4 are located within a wireless communication range of the receiving device 1 and the endoscopes 3 and 4 are powered on at the same timing, there arises a problem in that the endoscope 4 is erroneously connected with the receiving device 1.

The present invention is made in light of the above described problems and has an object to provide a wireless communication terminal that can prevent an erroneous connection of wireless communication.

Means for Solving the Problems

The present invention provides a wireless communication terminal that performs wireless communication with other terminal and includes an information holding unit that holds a communication channel setting of the wireless communication and information of a communication attribute of the wireless communication, a communication unit that receives the information of the communication attribute held by the other terminal from the other terminal by wireless communication using a communication channel that the communication channel setting held by the information holding unit represents before a logical connection of the wireless communication with the other terminal is established, and a control unit that controls the establishment process of the logical connection with the other terminal based on the information of the communication attribute received by the communication unit.

Further, in the wireless communication terminal of the present invention, when it is detected that a terminal that holds the same communication channel setting and communication attribute as the own terminal exists or when it is detected that a plurality of terminals that hold the same communication channel setting as the own terminal exist, the control unit may suspend the establishment process of the logical connection with the other terminal.

Further, the wireless communication terminal of the present invention may further include an informing unit that informs an operator of information representing a suspension of the establishment process when the control unit suspends the establishment process of the logical connection with the other terminal.

Further, in the wireless communication terminal of the present invention, the informing unit may further inform the operator of information encouraging a change of the communication channel setting.

Further, in the wireless communication terminal of the present invention, the information of the communication attribute may be information representing an attribute of any one of a terminal that establishes the logical connection with the other terminal in response to a connection request of wireless communication from the other terminal and a terminal that establishes the logical connection with the other terminal by making the connection request of the wireless communication for the other terminal.

Effects of the Invention

According to the present invention, among other terminals, only a terminal that has the same communication channel setting as the present wireless communication terminal transmits information of a communication attribute to the present wireless communication terminal. By controlling an establishment process of logical connection with the other terminals based on the information of the communication attribute, an erroneous connection of wireless communication can be prevented.

BRIEF DESCRIPTION OF THE DRAWINGS

FIG. 7 is a reference diagram illustrating the content of a communication setting parameter according to an embodiment of the present invention.

FIG. 8A is a reference diagram illustrating the content of a search request packet according to an embodiment of the present invention.

FIG. 8B is a reference diagram illustrating the content of the search request packet according to an embodiment of the present invention.

BEST MODE FOR CARRYING OUT THE INVENTION

Figure 1:
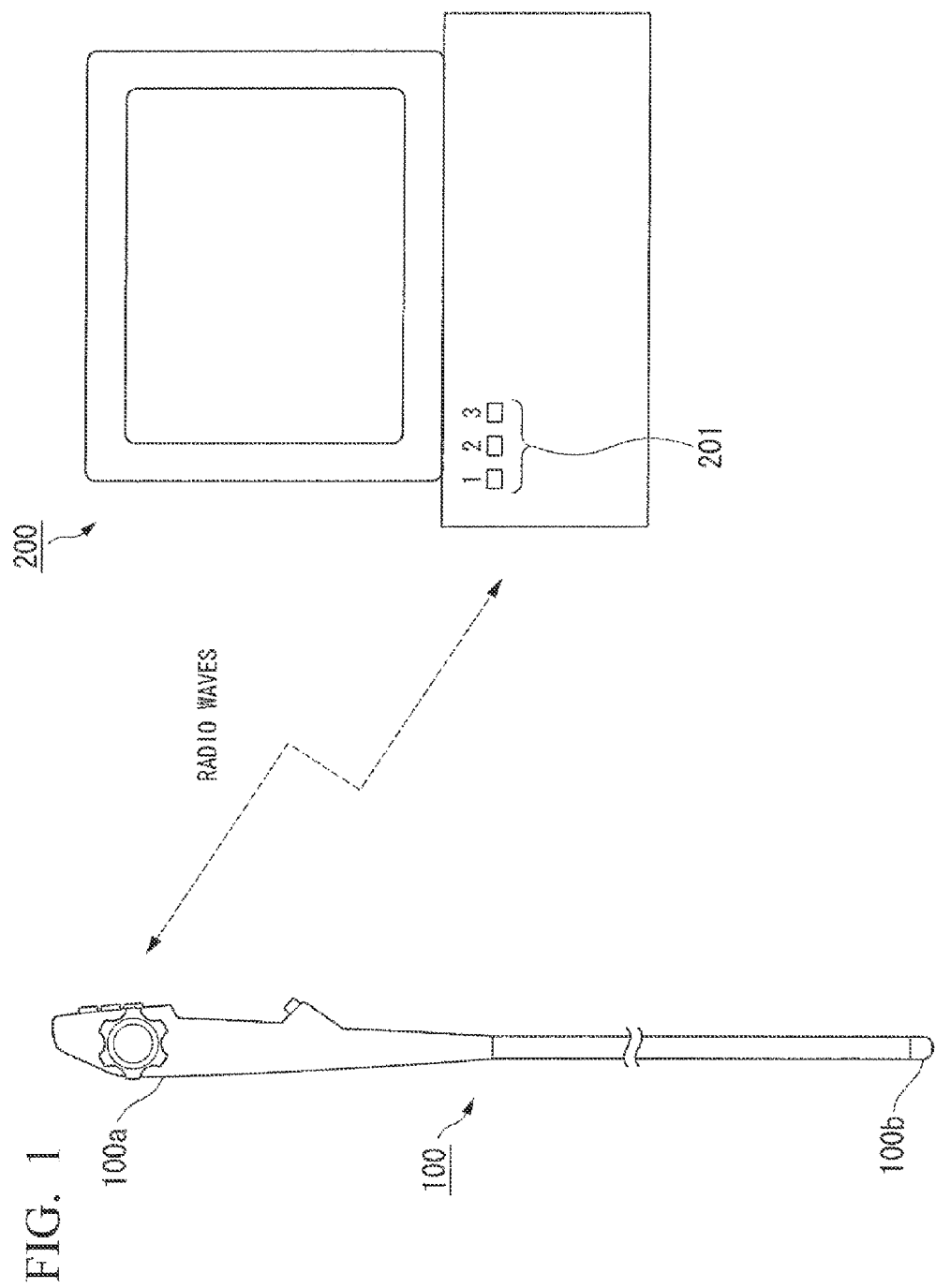
FIG. 1 is a configuration diagram illustrating a configuration of an endoscopic device according to an embodiment of the present invention.

Hereinafter, embodiments of the present invention will be described with reference to the accompanying drawings. In the present embodiment, as an example of a wireless communication scheme, IEEE 802.11, which is a wireless LAN protocol, is used. FIG. 1 illustrates a configuration of an endoscopic device according to the present invention. The endoscopic device includes an endoscope 100 that transmits captured image data by wireless communication and a receiving device 200 that receives the image data transmitted from the endoscope 100 and displays an image on a monitor. The endoscope 100 includes an operation unit 100*a* that includes a plurality of switches through which an operator inputs an operation instruction. The receiving device 200 includes a communication setting display unit 201 that includes a plurality of LEDs representing a communication setting status of the receiving device 200.

Figure 2:
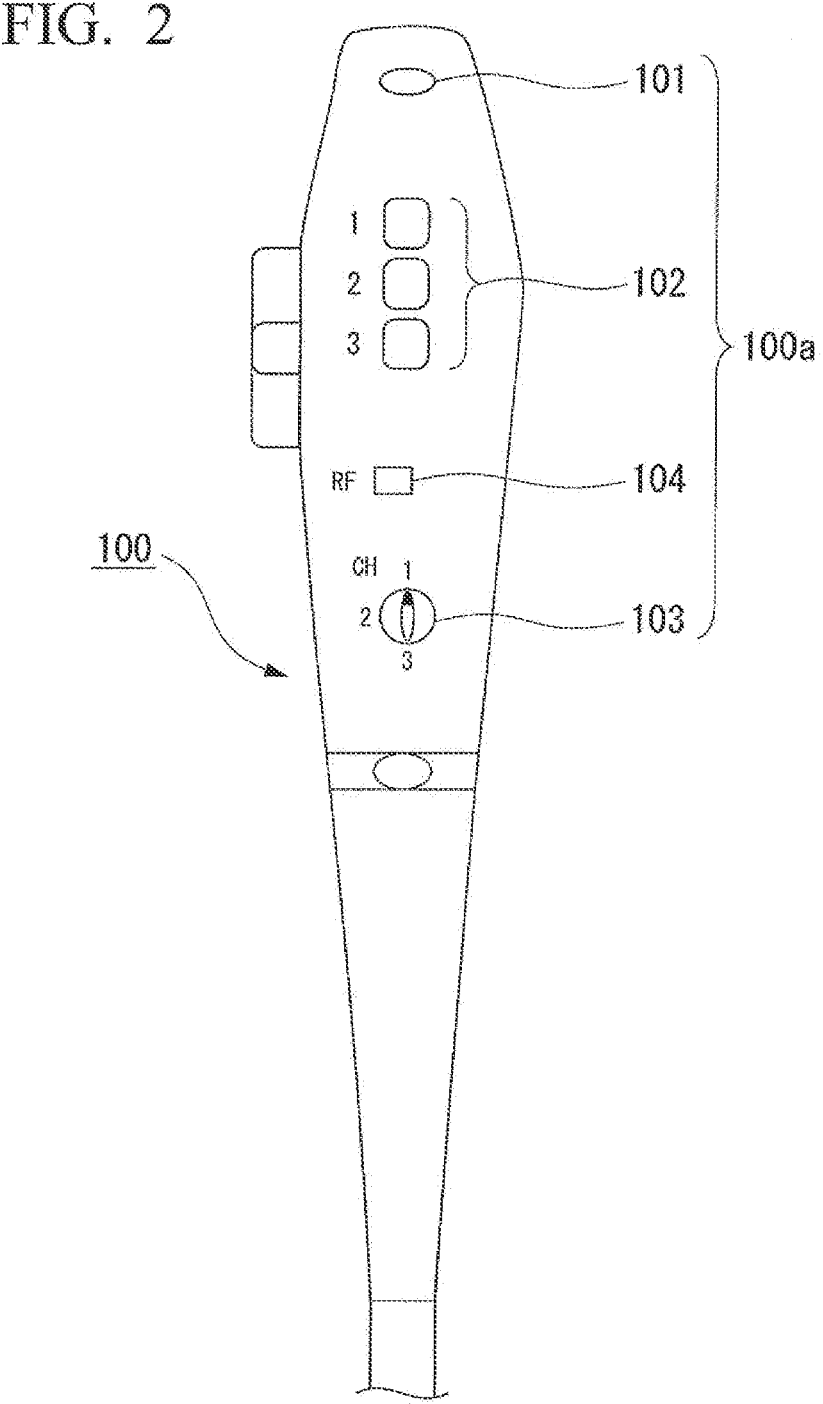
FIG. 2 is an appearance diagram of an endoscope according to an embodiment of the present invention.

FIG. 2 illustrates a status in which the endoscope 100 is viewed from an arrangement surface of an operation switch. The operation unit 100*a* of the endoscope 100 includes a power switch 101, a plurality of operation switches 102, a channel (CH) setting switch 103, and a status display LED 104. Numbers for identifying setting channels are added to the CH setting switch 103. The status display LED 104 includes an LED that can display two colors (green and orange).

Figure 3:
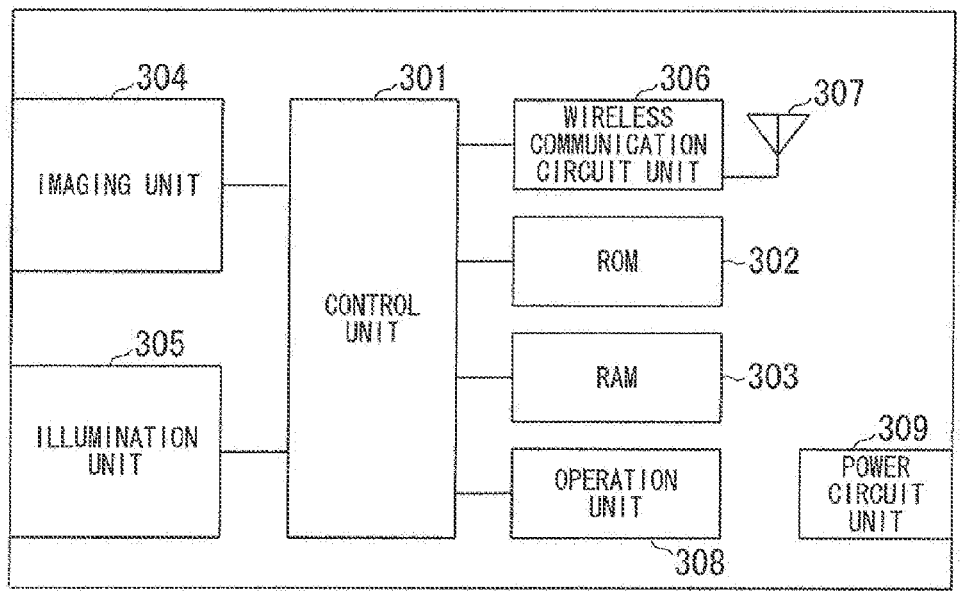
FIG. 3 is a block diagram illustrating a configuration of the endoscope according to an embodiment of the present invention.

FIG. 3 illustrates an electrical configuration of the endoscope 100. The endoscope 100 includes a control unit 301, a read only memory (ROM) 302, a random access memory (RAM) 303, an imaging unit 304, an illumination unit 305, a wireless communication circuit unit 306, an antenna 307, an operation unit 308, and a power circuit unit 309.

The control unit 301 operates according to a program stored in the ROM 302 and controls an operation sequence of the endoscope 100. The ROM 302 is a non-volatile memory such as a flash ROM. Various setting information including program data for controlling the endoscope 100 and a communication setting parameter is stored in the ROM 302.

FIG. 7 illustrates the content of the communication setting parameter. Each of the numbers added to the CH setting switch 103 is associated with a communication channel (frequency), a service set identifier (SSID), and a wired equivalent privacy (WEP).

The RAM 303 is used as a buffer for temporarily buffering image data output from the imaging unit 304, a work area used for a calculation of the control unit 301 or the like, and an area for temporarily storing various settings or the like. The RAM 303 is also used as an area for storing a communication setting parameter and information of a communication attribute. The information of the communication attribute refers to information for identifying which one of the endoscope 100 and the receiving device 200 the communication attribute represents. The endoscope 100 of the present embodiment transmits a wireless communication connection request to the receiving device 200, and thus a logical connection with the receiving device 200, which will be described later, is established. Further, the receiving device 200 of the present embodiment establishes the logical connection with the endoscope 100 in response to the wireless communication connection request from the endoscope 100.

The imaging unit 304 includes a lens for imaging incident light, a photoelectric converter (a charge coupled device (CCD) sensor, a complementary metal oxide semiconductor (CMOS) sensor, or the like) for converting imaged light to an electrical signal, an analog-digital (AD) converter for converting an analog electrical signal output from the photoelectric converter to a digital electrical signal, and the like.

The illumination unit 305 includes an irradiation lens, an LED, an LED driving circuit, and the like and is disposed in a tip section 100b (FIG. 1) of the endoscope 100. Light emitted from the LED is irradiated to an observation target within the body cavity through the irradiation lens. The LED may be disposed inside the operation unit 100a rather than the tip section 100b, and light may be guided to the tip section 100b through a light guide.

The wireless communication circuit unit 306 includes a high frequency circuit unit necessary for wireless communication, an encoding/decoding circuit unit, a buffer memory, and the like and is connected with the antenna 307. In order to perform the wireless communication with the receiving device 200, it is necessary to set the communication channel, the communication channel which is the same as the SSID and the like, the SSID, and the like set for the receiving device 200.

The operation unit 308 (that corresponds to the operation unit 100a of FIG. 1) includes the power switch 101, the operation switch 102, and the CH setting switch 103 that are illustrated in FIG. 2 and outputs a status and a status change of the buttons and the switches as an electrical signal. Further, the status display LED 104 that informs of a connection status with the receiving device 200 is disposed in the operation unit 308.

The power circuit unit 309 includes a battery, a DC/DC converter, and the like. The power circuit unit 309 detects that the power switch 101 is turned on and supplies the above described blocks with electric power.

Figure 4:
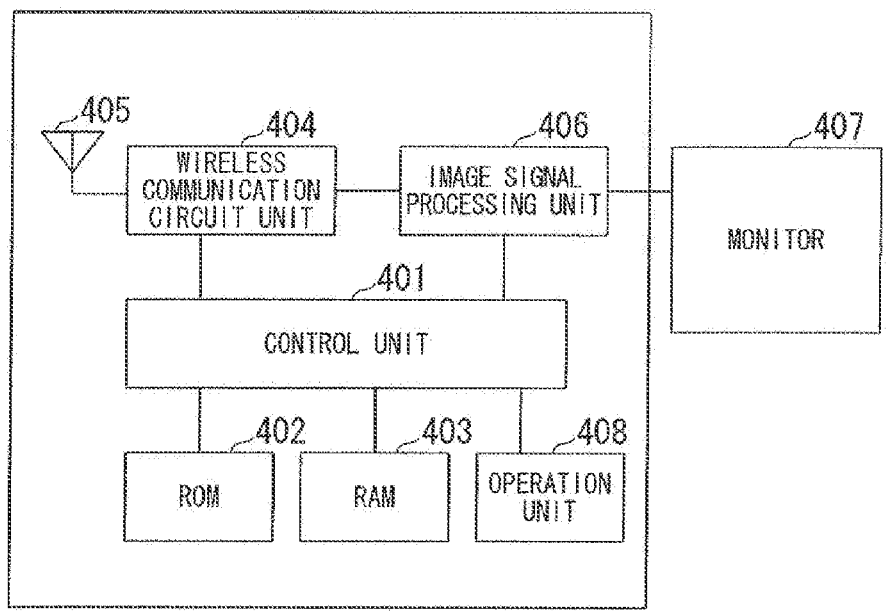
FIG. 4 is a block diagram illustrating a configuration of a receiving device according to an embodiment of the present invention.

FIG. 4 illustrates an electrical configuration of the receiving device 200. The receiving device 200 includes a control unit 401, a ROM 402, a RAM 403, a wireless communication circuit unit 404, an antenna 405, an image signal processing unit 406, a monitor 407, and an operation unit 408.

The control unit 401 operates according to a program stored in the ROM 402 and controls an operation sequence of the receiving device 200. The ROM 402 is a non-volatile memory such as a flash ROM. Various setting information including program data for controlling the receiving device 200 and a communication setting parameter is stored in the ROM 402.

The ROM 403 is used as a buffer for temporarily buffering image data received by the wireless communication circuit unit 404, a work area used for a calculation of the control unit 401 or the like, and an area for temporarily storing various settings or the like. The RAM 403 is also used as an area for storing the communication setting parameter and the information of the communication attribute.

The wireless communication circuit unit 404 includes a high frequency circuit unit necessary for wireless communication, an encoding/decoding circuit unit, a buffer memory, and the like and is connected with the antenna 405. The wireless communication circuit unit 404 performs the wireless communication according to the wireless LAN protocol similarly to the wireless communication circuit unit 306 of the endoscope 100.

The image signal processing unit 406 converts the image data received by the wireless communication circuit unit 404 into an NTSC signal or a PAL signal and outputs the NTSC signal or the PAL signal to the monitor 407. The monitor 407 includes a liquid crystal display device and a control circuit thereof. The monitor 407 displays an image and functions as an informing unit for informing of a wireless connection status.

The operation unit 408 includes a CH setting switch (not shown in FIG. 1) mounted on a back side of the receiving device 200 and outputs a status and a status change of the CH setting switch as an electrical signal. Further, the communication setting display unit 201 (FIG. 1) that displays the communication channel selected by the CH setting switch through an LED is disposed in the operation unit 408.

Next, an operation of the receiving device 200 according to the present embodiment will be described with reference to FIG. 5. The operator performs setting of the communication channel through the CH setting switch of the receiving device 200 and thereafter turns on the power of the receiving device 200. When the power of the receiving device 200 is turned on, the control unit 401 initializes the function blocks of the receiving device 200 (step S501).

Subsequently, the control unit 401 stores the communication setting parameter including communication channel settings set by the CH setting switch and the information of the communication attribute of the receiving device 200 in the RAM 403. In the communication setting display unit 201, an LED corresponding to the set communication channel is turned on (step S502). Subsequently, the control unit 401 initializes values T and R for counting the communication terminals of the communication attributes to zero (0) (step S503).

Subsequently, the receiving device 200 performs a physical connection of the wireless communication through the communication channel selected by the operator. In the physical connection, a wireless frequency used for a connection in a physical layer and the SSID are decided, and the receiving device 200 becomes a state capable of fetching a packet transmitted and received with a communication partner onto hardware. First, the receiving device 200 shifts to a search phase of the communication terminal (the endoscope 100 or the receiving device 200).

For the search of the communication terminal, a search request packet is transmitted, and receipt of a search request response packet on the search request packet is performed during a predetermined time period. The control unit 401 transmits the search request packet to the wireless communication circuit unit 404 in a broadcast manner (step S504). FIG. 8A illustrates the content of the search request packet. First a header 800, and then an SSID 801, a supported communication rate 802, and a frame check sequence (FCS) 803 are stored.

The communication terminal for which the same communication channel as the receiving device 200 is set receives the search request packet transmitted from the receiving device 200 and transmits the search request response packet. FIG. 8B illustrates the content of the search request response packet. First a header 810, and then an SSID 811, a supported communication rate 812, a communication attribute 813, and a FCS 814 are stored. The communication attribute 813 is "0" when the communication terminal that is a transmission source of the search request response packet is the receiving device 200 and "1" when the communication terminal that is the transmission source of the search request response packet is the endoscope 100. In the physical connection, the wireless communication is performed using the communication channel represented by communication channel settings stored in the RAM 403.

After transmitting the search request packet, the control unit 401 determines whether or not the search request response packet has been received (step S505). When the search request response packet has not been received, the process proceeds to step S509. When the search request response packet has been received, the control unit 401 determines the communication attribute included in the search request response packet (step S506).

When the communication attribute represents the receiving device, the control unit 401 increases the value R by one (1) (step S507). When the communication attribute represents the endoscope, the control unit 401 increases the value T by one (1) (step S508).

Subsequently, the control unit 401 determines whether or not the search request packet has been received (step S509). When the search request packet has been received, the control unit 401 transmits the search request response packet to the wireless communication circuit unit 404 in a unicast manner (step S510).

When the search request packet has not been received, the control unit 401 determines whether or not a predetermined time period has elapsed since the search request packet has been transmitted in step S504 (step S511). Also, after each process of steps S507, S508 and S509 is performed, the process proceeds to step S511. When the predetermined time period has not elapsed, the process returns to step S505. When the predetermined time period has elapsed, the control unit 401 determines whether or not the sum of the values R and T is zero (0) (step S512).

If the sum of the values R and T is zero (0), it means that there is no communication terminal within the communication range of the receiving device 200. In this case, the process returns to step S504, and the search of the communication terminal is performed again. If the sum of the values R and T is not zero (0), it means that there is another communication terminal within the communication range of the receiving device 200. In this case, the control unit 401 determines whether or not the value R is greater than or equal to one (1) (step S513).

Figure 9:
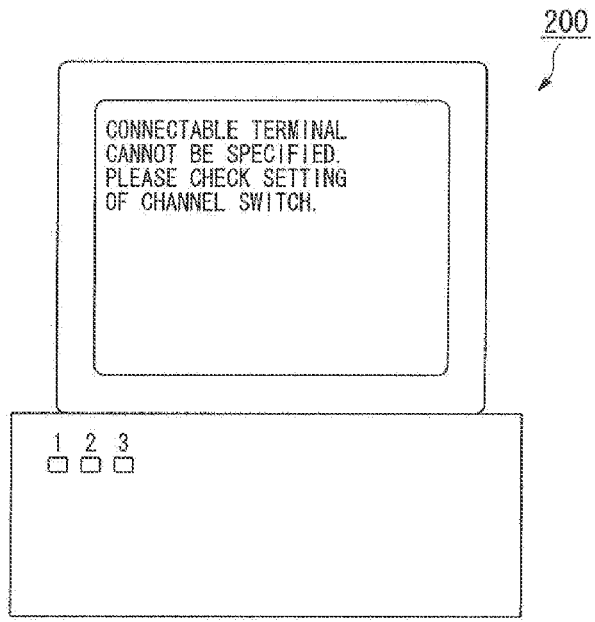
FIG. 9 is a reference diagram illustrating the content of a search request response packet according to an embodiment of the present invention.
Figure 10:
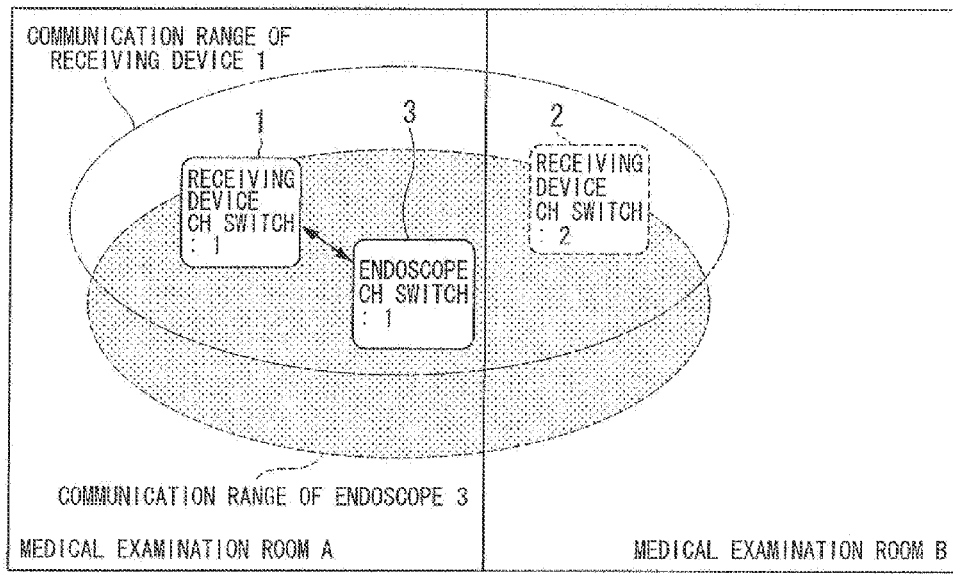
FIG. 10 is a reference diagram for explaining a problem of a conventional art.
Figure 11:
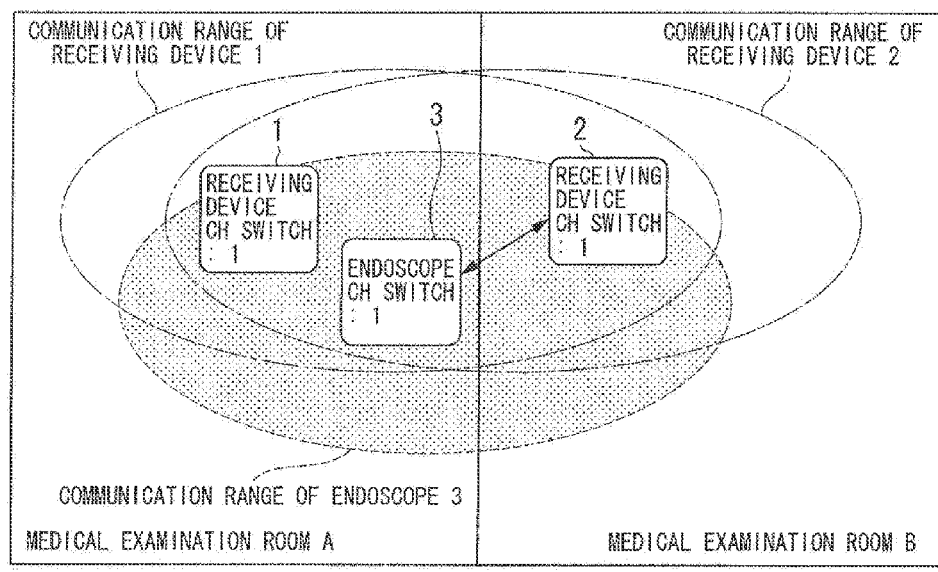
FIG. 11 is a reference diagram for explaining a problem of a conventional art.
Figure 12:
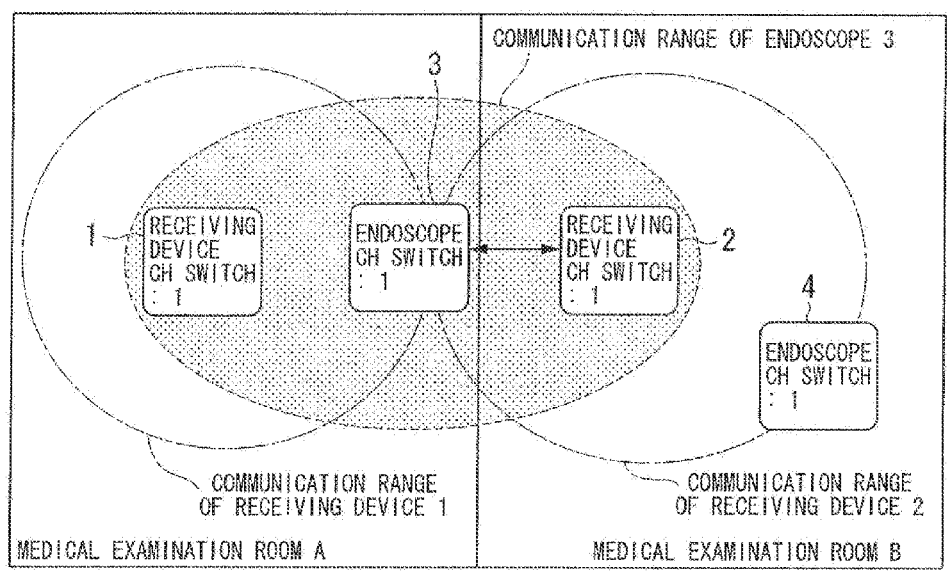
FIG. 12 is a reference diagram for explaining a problem of a conventional art.
Figure 13:
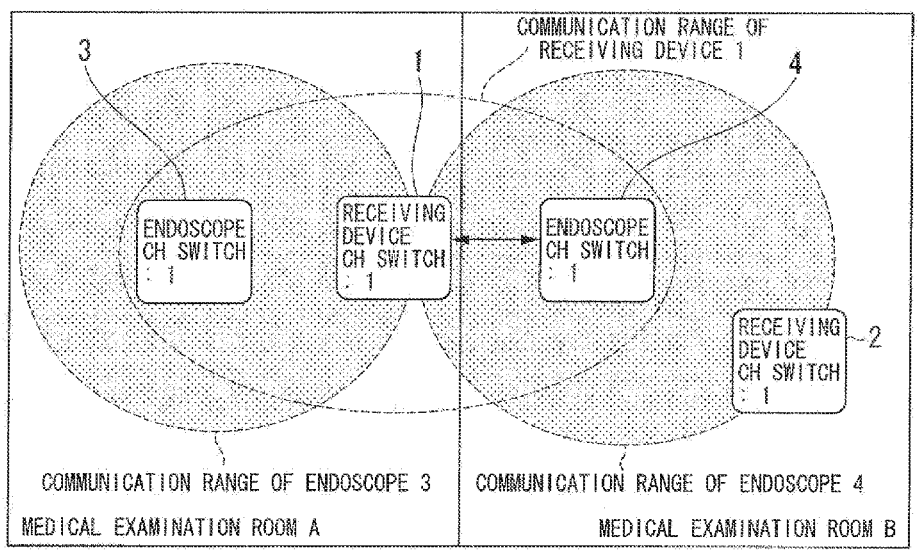
FIG. 13 is a reference diagram for explaining a problem of a conventional art.

When the value R is greater than or equal to one (1), it means that there is another receiving device 200 for which the same communication channel is set within the communication range of the receiving device 200. In this case, the control unit 401 executes a process for displaying an alarm on the image signal processing unit 406 and outputs an image signal for displaying an alarm to the monitor 407. As a result, an alarm is displayed on the monitor (step S517). FIG. 9 illustrates an example of an alarm displayed on the monitor 407 of the receiving device 200.

Subsequently, the control unit 401 determines whether or not the communication channel in the CH setting switch has changed (step S518). When the communication channel has not changed, the process of step S517 is performed again. When the communication channel has changed, the process returns to step S502.

Meanwhile, when it is determined in step S513 that the value R has been less than one (1) (that is, 0), the control unit 401 determines whether or not the value T is larger than one (1) (step S514). When the value T is larger than one (1), it means that there are a plurality of endoscopes 100 for which the same communication channel is set. In this case, the process proceeds to step S517, and an alarm is displayed on the monitor 407 of the receiving device 200.

When the value T is greater than or equal to 1, since the sum of the values R and T is not zero (0) and the value R is 0, the value T is 1. In this case, it means that there is one endoscope 100 for which the same communication channel is set within the communication range of the receiving device 200. As a result, the receiving device 200 shifts to a logical connection phase and executes a process for establishing the logical connection (step S515).

The logical connection is a status in which a combination of two specific communication terminals, that is, the endoscope 100 and the receiving device 200, among a plurality of communication terminals that are physically connected is decided. In the present embodiment, when the logical connection is completed, a destination (a MAC address) to which the endoscope 100 transmits the image data is decided. In the logical connection phase, the endoscope 100 transmits a MAC address request packet including a MAC address of the endoscope 100. The receiving device 200 that has received the MAC address request packet transmits a MAC address request response packet including a MAC address of the receiving device 200. As a result, the MAC addresses are exchanged between the endoscope 100 and the receiving device 200.

When the logical connection is completed, the receiving device 200 starts to receive the image data transmitted from the endoscope 100 (step S516). According to the above described operation, since the logical connection is established when only one endoscope 100 for which the same communication channel is set exists within the communication range of the receiving device 200, an erroneous connection of the wireless communication can be prevented.

Next, an operation of the endoscope 100 according to the present embodiment will be described with reference to FIG. 6. The operator performs setting of the communication channel by the CH setting switch 103 of the endoscope 100 according to the communication channel displayed by the communication setting display unit 201 of the receiving device 200. Thereafter turns on the power of the endoscope 100. When the power of the endoscope 100 is turned on, the control unit 301 initializes the function blocks of the endoscope 100 (step S601).

Figure 5:
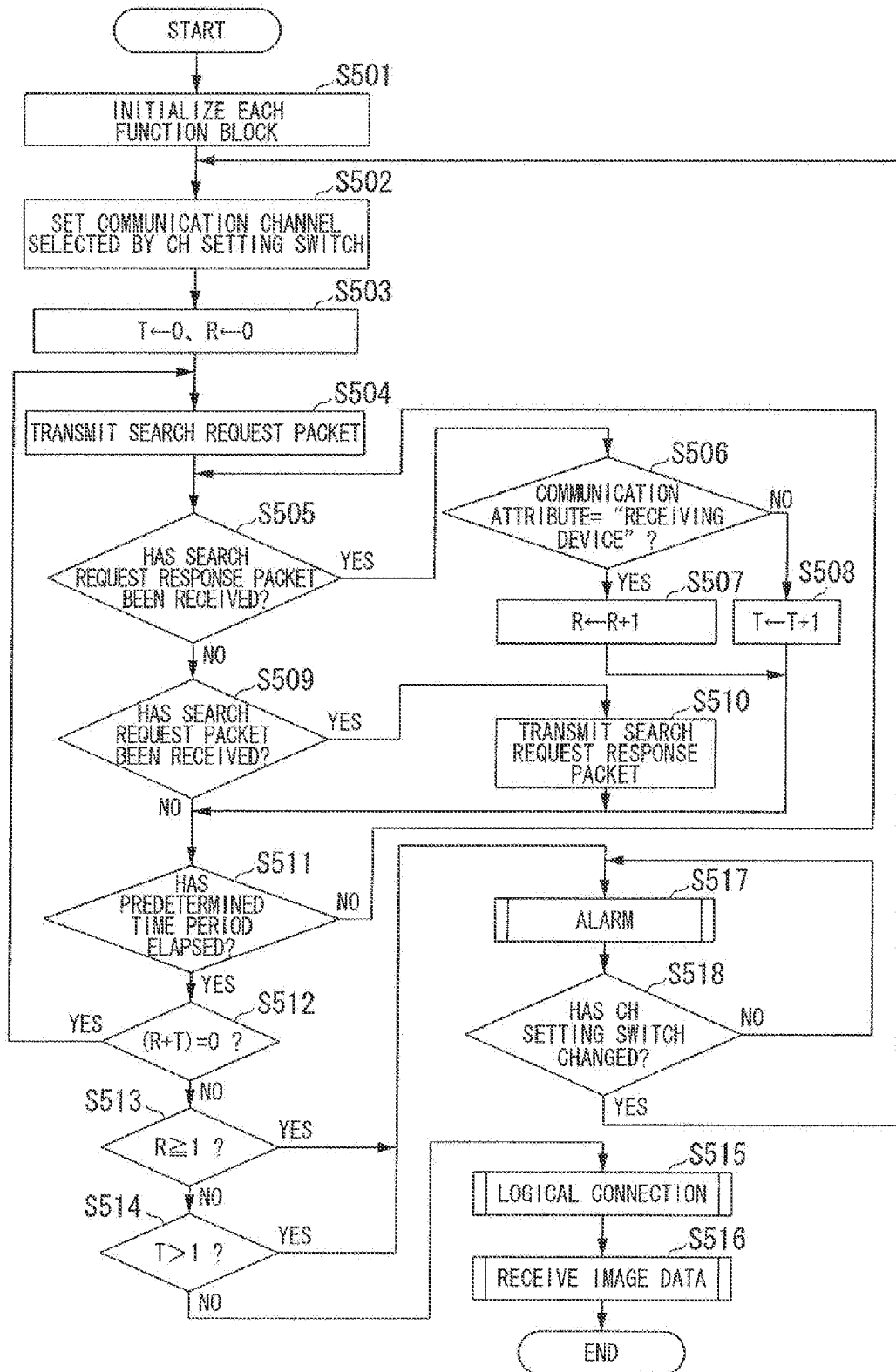
FIG. 5 is a flowchart illustrating an operation of the receiving device according to an embodiment of the present invention.

Processes of step S602 to step S612 are similar to the processes of step S502 to step S512 of FIG. 5, and thus a description thereof will be omitted. When it is determined in step S612 that the sum of the values R and T is not zero (0), it means that another communication terminal exists in the communication range of the endoscope 100. In this case the control unit 301 determines whether the value T is greater than or equal to one (1) (step S613). When the value T is greater than or equal to one (1), it means that there is another endoscope 100 for which the same communication channel is set. In this case, in order to inform the operator of an alarm, the control unit 301 turns on the status display LED 104 to light up or blink orange (step S617).

Subsequently, the control unit 301 determines whether or not the communication channel in the CH setting switch 103 has changed (step S618). When the communication channel has not changed, the process of step S617 is performed again. Further, when the communication channel has changed, the process returns to step S602 again.

Meanwhile, when the value T is less than one (1) (that is, zero (0)), it means that another endoscope 100 for which the same communication channel is set does not exist in the communication range of the endoscope 100. In this case, the control unit 301 determines whether or not the value R is larger than one (1) (step S614). When the value R is larger than one (1), it means that there are a plurality of receiving devices 200 for which the same communication channel is set. In this case, the process proceeds to step S617, and the status display LED 104 informs the operator of an alarm.

When the value R is greater than or equal to one (1), since the sum of the values R and T is not zero (0) and the value T is zero (0), the value R is one (1). In this case, it means that only one receiving device 200 for which the same communication channel is set exists in the communication range of the endoscope 100. As a result, the endoscope 100 shifts to the logical connection phase and executes the process of establishing the logical connection (step S615). When the logical connection is completed, the endoscope 100 starts to transmit the image data to the receiving device 200 (step S616). According to the above described operation, since the logical connection is established when only one receiving device 200 for which the same communication channel is set exists within the communication range of the endoscope 100, an erroneous connection of the wireless communication can be prevented.

As described above, according to the present embodiment, in the endoscope 100 or the receiving device 200, when only one communication terminal that holds the same communication channel setting as the own terminal and holds a different communication attribute is detected, the logical connection establishment process is executed. Further, in the endoscope 100 or the receiving device 200, when it is detected that the communication terminal that holds the same communication channel setting and communication attribute as the own terminal exists or when it is detected that a plurality of communication terminals that hold the same communication channel setting exist, the logical connection establishment process is suspended. As a result, an erroneous connection of the wireless communication can be prevented.

Figure 6:
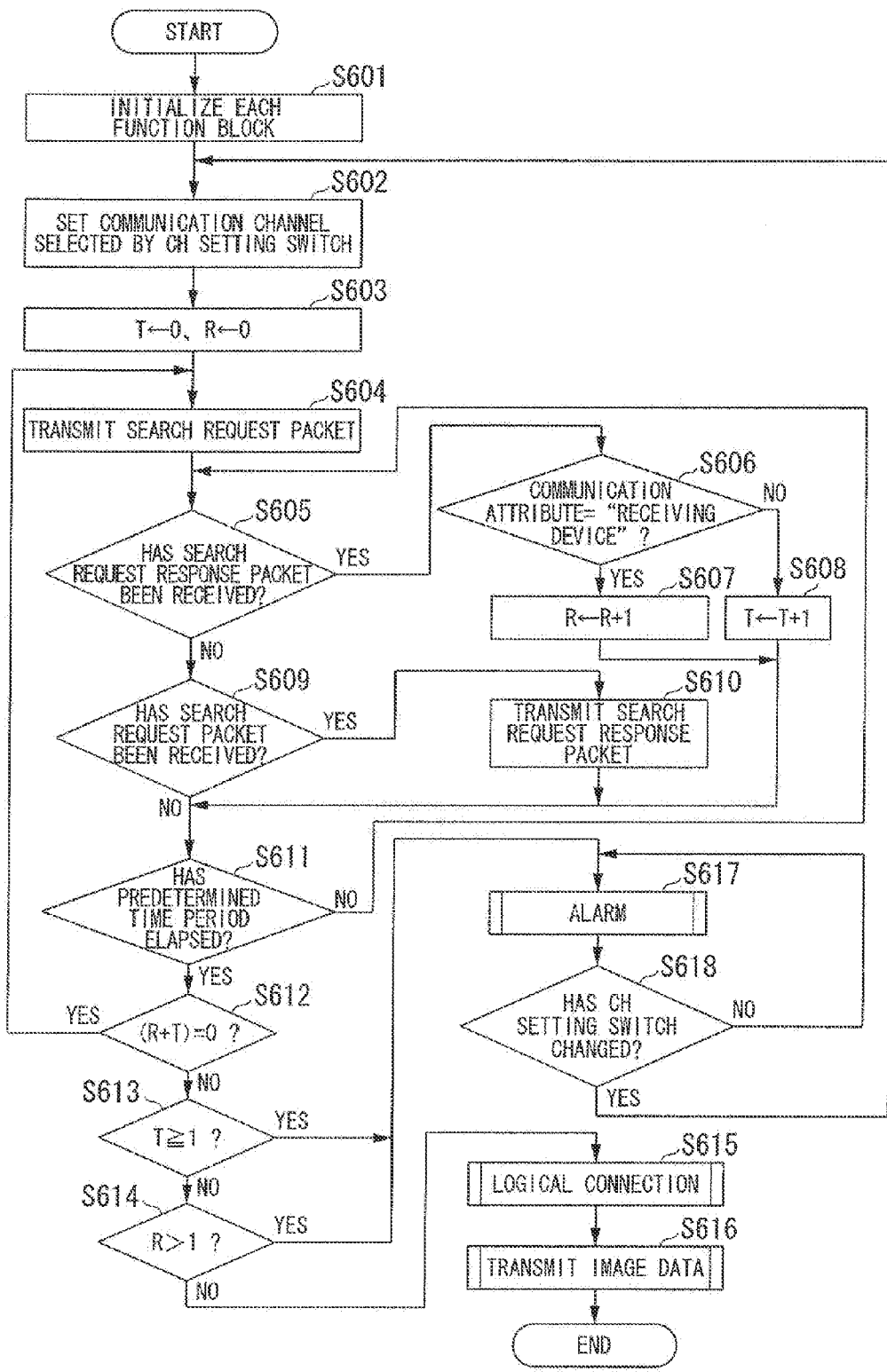
FIG. 6 is a flowchart illustrating an operation of the endoscope according to an embodiment of the present invention.

When the logical connection establishment process is suspended, the operator is informed of information representing the suspension of the establishment process and information encouraging a change of communication channel settings (step S517 of FIG. 5 and step S617 of FIG. 6). Thus, the operator can recognize that the endoscope 100 is not normally wirelessly connected with the receiving device 200, and the operator can be encouraged to change communication channel settings.

The embodiments of the present invention have been described above, but a concrete configuration is not limited to the above embodiments, and a design change or the like may be made within a range that does not depart from the scope of the present invention.

INDUSTRIAL APPLICABILITY

According to the present embodiment, among other terminals, only a terminal that has the same communication channel setting as the present wireless communication terminal transmits information of a communication attribute to the present wireless communication terminal. By controlling an establishment process of logical connection with another terminal based on the information of the communication attribute, an erroneous connection of wireless communication can be prevented.

DESCRIPTION OF REFERENCE NUMERALS

100: Endoscope (wireless communication terminal)
101: Power switch
102: Operation switch
103: CH setting switch
104: Status display LED (informing unit)
200: Receiving device (wireless communication terminal)
201: Communication setting display unit
301, 401: Control unit
302, 402: ROM
303, 403: RAM (information holding unit)
304: Imaging unit
305: Illumination unit
306, 404: Wireless communication circuit unit (communication unit)
307, 405: Antenna
308, 408: Operation unit
406: Communication setting display unit
407: Monitor (informing unit)

The invention claimed is:

1. A wireless communication terminal that performs wireless communication with other terminal, comprising:
an information holding unit that holds a communication channel setting of the wireless communication and information of a communication attribute of the wireless communication;
a communication unit that receives the information of the communication attribute held by one or a plurality of the other terminals or others from one or a plurality of the other terminals by wireless communication using a communication channel that the communication channel setting held by the information holding unit represents before a logical connection of the wireless communication with one or a plurality of the other terminals is established;
a control unit that controls whether or not the establishment process of the logical connection with one or a plurality of the other terminals based on the information of the communication attribute of one or a plurality of the other terminals received by the communication unit is suspended during a predetermined time period wherein, when the control unit detects that a terminal that holds the same communication channel setting and the same communication attribute as the own terminal exists, or when the control unit detects that a plurality of terminals that hold the same communication channel setting as the own terminal exist, the control unit suspends the establishment process of the logical connection with the other terminal; and
an informing unit that informs an operator of information representing a suspension of the establishment process when the control unit suspends the establishment process of the logical connection with the other terminal.

2. The wireless communication terminal according to claim 1, wherein the informing unit further informs the operator of information encouraging a change of the communication channel setting.

3. The wireless communication terminal according to claim 1, wherein the information of the communication attribute is information representing an attribute of any one of a terminal that establishes the logical connection with the other terminal in response to a connection request of wireless communication from the other terminal and a terminal that establishes the logical connection with the other terminal by making the connection request of the wireless communication for the other terminal.

* * * * *